US00PP30089P2

(12) United States Plant Patent
Cain

(10) Patent No.: US PP30,089 P2
(45) Date of Patent: Jan. 15, 2019

(54) GRAPEVINE NAMED 'IFG TWENTY-EIGHT'

(50) Latin Name: ***Vitis interspecific* hybrid**
Varietal Denomination: IFG Twenty-eight

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/731,723

(22) Filed: Jul. 24, 2017

(51) Int. Cl.
*A01H 5/08* (2018.01)

(52) U.S. Cl.
USPC ..... Plt./207
CPC ..... *A01H 5/08* (2013.01)

(58) Field of Classification Search
USPC ..... Plt./207
CPC ..... A01H 5/0812
See application file for complete search history.

*Primary Examiner* — Kent L Bell

(57) ABSTRACT

This invention is a new and distinct grapevine variety denominated 'IFG Twenty-eight'. The new grapevine is characterized by producing naturally medium large, round to slightly elliptic, seedless berries having a small seed trace that is normally not noticeable. Berries are medium firm in texture and ripen in mid-season. Fruits normally ripen in early August, about with or just slightly earlier than the Thompson Seedless variety near Delano, Calif.

1 Drawing Sheet

Latin name of the genus and species claimed: *Vitis interspecific* hybrid.

Variety denomination: 'IFG Twenty-eight'.

BACKGROUND OF THE INVENTION

The new and distinct grapevine plant described and claimed herein originated from a hand pollinated cross of the 01032-067-202, an unnamed seedling selection from IFG breeding program, and 03095-048-036, an unnamed interspecific seedling from the IFG breeding program, hybridized in May 2006. The abortive seed traces were subsequently embryo cultured and the resulting population of ninety-nine plants was planted in the field in April 2007. The present variety of grapevine was selected as a single plant in October 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Twenty-eight' is characterized by producing naturally medium large, round to slightly elliptic, seedless berries having a small seed trace that is normally not noticeable. Berries are medium firm in texture and ripen in mid-season. Fruits normally ripen in early August, about with or just slightly earlier than the Thompson Seedless variety near Delano, Calif.

To the inventor's knowledge, the known variety which the new grapevine variety is most similar to is its parent the 01032-067-202 variety. 'IFG Twenty-eight' can be distinguished from the 01032-067-202 variety by having a slightly more elliptic shape as opposed to the more completely round shape of the 01032-067-202 variety. The ripening time of the 'IFG Twenty-eight' is earlier than that of the 01032-067-202 variety; it ripening in early August while the 01032-067-202 ripens in early September. The 'IFG Twenty-eight' is somewhat prone to bruising and browning, is very productive and produces large clusters of naturally medium large berries.

The 'IFG Twenty-eight' differs from its pollen parent, the 03095-048-036 by producing more round to slightly elliptic berries as opposed to the more oval berries of the 03095-048-036 variety.

Commercial grape growers perform many cultural manipulations to produce crops of commercially acceptable fruit. Many of these cultural manipulations are difficult for home owners and non-commercial growers to perform. The new grapevine variety 'IFG Twenty-eight' is being introduced to provide non-commercial growers with a grape variety that produces large clusters of naturally medium large, medium firm berries that is easy to grow.

BRIEF DESCRIPTION OF THE DRAWING

The accompanying photographic drawing in FIG. 1 illustrates in full color 'IFG Twenty-eight', taken from a 6-year-old vine. The photograph was taken outdoors with indirect lighting. The colors are as nearly true as is reasonably possible in a color representation of this type. The left side of the figure has mature leaves. A mature fruit cluster is represented in the center of the drawing along with a typical berry in cross section. A young shoot tip with tendrils can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-eight' plants grown in the vicinity of Delano, Kern County, Calif. during 2015 and 2016, and is believed to apply to plants of the variety grown under similar conditions of soil and climate elsewhere:

VINE

General:

*Vigor*.—Moderately vigorous.
*Density of foliage*.—Moderate to somewhat dense.
*Productivity*.—Very productive producing about 34 to 51 kg of fruit per vine.
*Root stock*.—Own root.
*Training method*.—Typically spur pruned leaving 2 bud spurs.

Trunk:

*Trunk diameter of 6-year-old vines at 30 cm above the soil line*.—About 6.3 cm.
*Shape*.—Slender.
*Straps*.—Short — split.
*Surface texture*.—Shaggy.
*Inner bark color*.—Greyed-orange: 165A.
*Outer bark color*.—Brown: N200B.

SHOOTS

Young shoot:

*Form of tip*.—Wide open.
*Distribution and color of anthocyanin coloration of tip*.—Piping (striped) on young tendrils, Red-purple: 59B.
*Intensity of anthocyanin coloration of tip*.—Very weak.
*Density of prostrate hairs of tip*.—Dense.
*Density of erect hairs of tip*.—Absent.
*Color*.—Yellow-green: N144A.

Woody shoot (mature canes):

*Internode length*.—Short: About 10.1 cm.
*Width at node*.—About 1.3 cm.
*Cross section*.—Elliptic.
*Surface*.—Smooth to slightly striate.
*Main color*.—The following colors were observed: Greyed-orange: 164A and 164B and 175A.
*Density of erect hairs on nodes*.—None.
*Density of erect hairs on internodes*.—None.
*Growth of axillary shoots*.—Weak: About 4.0 cm.

Flowering shoot:

*Vigor during flowering*.—Strong.
*Attitude during flowering on shoots not tied*.—Erect.
*Color*.—Dorsal side of internodes — Yellow-green: 146C, with Red-purple stripes: 59B.
*Color*.—Ventral side of internodes — Yellow-green: 146C.
*Color*.—Dorsal side of nodes — Yellow-green: 146C.
*Color*.—Ventral side of nodes — Yellow-green: 146C.
*Density of prostrate hairs of nodes*.—Very sparse.
*Density of erect hairs on nodes*.—None.
*Density of prostrate hairs on internode*.—Very sparse.
*Density of erect hairs on internode*.—None.
*Anthocyanin coloration of buds*.—Absent.

Tendrils:

*Distribution on the shoot (at full flowering)*.—Discontinuous.
*Length of tendril*.—Long: About 22.4 cm.
*Thickness of tendril 2 cm from base*.—About 3.1 cm.
*Color*.—Yellow-green: N144 A.
*Form*.—Combination of bifurcated and trifurcated.
*Number of consecutive tendrils*.—2.

LEAVES

Young leaves:

*Color of upper surface of first four distal unfolded leaves*.—Yellow-green: 146A.
*Color of lower surface of young leaves*.—Yellow-green: 144A.
*Average intensity and color of anthocyanin coloration of six distal leaves prior to flowering*.—Very weak: Red-purple: 59B.
*Density of prostrate hairs between veins (lower surface)*.—Sparse.
*Density of prostrate hairs on veins (lower surface)*.—Sparse.
*Density of erect hairs between veins (lower surface)*.—Absent.
*Density of erect hairs on veins (lower surface)*.—Very sparse.

Mature leaves:

*Average length*.—About 12.3 cm.
*Average width*.—About 17.0 cm.
*Mature leaf size*.—Large.
*Shape of blade*.—Wedge-shaped.
*Number of lobes*.—5.
*Venation*.—Palmate.
*Anthocyanin coloration of main veins on upper side of blade*.—Weak.
*Mature leaf profile*.—Undulate.
*Blistering surface of blade upper surface*.—Medium.
*Leaf apex*.—Broadly acute.
*Leaf blade tip*.—In the plane of the leaf.
*Leaf margin*.—Serrate.
*Undulation of margin*.—Moderate.
*Undulation of blade between main and lateral veins*.—Over entire.
*Shape of teeth*.—Mixture of both sides straight and both sides convex.
*Length of teeth*.—Medium.
*Ratio length/width of teeth*.—Medium.
*Shape of upper lateral sinuses*.—Lobes slightly overlapping.
*Depth of upper lateral sinuses*.—Medium.
*General shape petiole sinus*.—Wide open.
*Shape of base of upper leaf sinuses*.—V-shaped.
*Tooth at petiole sinus*.—Absent.
*Density of prostrate hairs between veins on lower surface of blade*.—Sparse.
*Density of erect hairs between veins on lower surface of blade*.—Sparse to medium.
*Density of prostrate hairs on main veins on lower surface of blade*.—Medium.
*Density of erect hairs on main veins on lower surface of blade*.—Sparse.

*Density of prostrate hairs on main veins on upper surface of blade*.—Sparse.
*Density of erect hairs on main veins on upper surface of blade*.—None.
*Autumn coloration of leaves*.—Leaves can be a single color or combination of colors, in a mottled pattern or on the edges of the leaves. The following colors were observed: Greyed-purple: N186B and N186C and 187A and 187B.

Upper surface:
*Color*.—Green: 137A.
*Color of main veins*.—The following colors were observed: Yellow-green: 145A and Red-purple: 181B.
*Anthocyanin coloration of main veins*.—Weak.
*Surface appearance*.—Dull.
*Blistering surface of blade*.—Medium.

Lower surface:
*Color*.—Yellow-green: 146B.
*Color of main veins*.—The following colors were observed: Yellow-green: 145A and Red-purple: 181B.
*Anthocyanin coloration of main veins* (*lower surface*).—Medium.
*Glossiness*.—Medium.
*Surface texture*.—Rugose.
*Surface appearance*.—Semi-glossy.

Petiole:
*Length*.—About 9.9 cm.
*Diameter of petiole 2 cm from blade*.—About 3.0 mm.
*Petiole color*.—The following colors were observed: Yellow-green: 144B and Greyed-red: 181A.
*Length of petiole compared to middle vein*.—Slightly shorter.
*Density of prostrate hairs on petiole*.—Sparse.
*Density of erect hairs on petiole*.—Very sparse.

Buds:
*Bud fruitfulness*.—Basal: Mostly fruitful.
*Dormant bud length*.—About 5.1 mm.
*Dormant bud width in the proximal/distal plane*.—About 5.5 mm.
*Dormant bud color*.—Greyed-orange: 166A.
*Position of first fruitful shoot on previous season cane*.—$1^{st}$ to $2^{nd}$ node.
*Time of bud burst*.—Approximately Mar. 3, 2016.

FLOWERS

General:
*Flower sex*.—Hermaphrodite.
*Length of single flower, unopened*.—About 2.8 mm.
*Width of single flower*.—Unopened: About 1.9 mm. Opened: About 7.3 mm.
*Stamen length*.—About 3.8 mm.
*Stamen count*.—5.
*Pollen color*.—Yellow: 10A.
*Pistil length*.—About 2.7 mm.
*Pistil color*.—Yellow-green: 144A.
*Length of first inflorescence*.—Long: About 23.2 cm long by 16.3 cm wide.
*Position of first flowering and fruiting node*.—$4^{th}$ to $5^{th}$ node (current season growth).
*Number of inflorescence per flowering shoot*.—1.1 to 2: About 2.
*Time of bloom*.—Medium as compared with similar varieties in the growing area of Delano, Calif.
*Date of full bloom*.—About Apr. 30, 2015.

FRUIT

General:
*Ripening period*.—Mid-season: Approximately Aug. 3, 2015.
*Use*.—Fresh market.
*Keeping quality*.—Good.
*Resistance to*.—Insects: Average typical of *Vitis vinifera* species. Diseases: Average typical of *Vitis vinifera* species.
*Refractometer test*.—Soluble solids: About 17.8 Brix.
*Brix/acid*.—About 29.2%.
*Titratable acidity*.—About 0.61.
*Juice ph*.—About 3.36.

Cluster:
*Mature cluster length* (*peduncle excluded*).—About 33.1 cm.
*Mature cluster width*.—About 17.7 cm.
*Mature cluster weight*.—About 1136 g.
*Bunch density*.—Medium.
*Number of berries*.—About 323.
*Form*.—Conical.

Peduncle:
*Lignification of peduncle*.—Moderate.
*Diameter of peduncle*.—About 7.0 mm.
*Length of peduncle*.—Medium, Approximately 3.4 cm.
*Color of peduncle*.—Yellow-green: 144C.

Berry:
*Uniformity of size*.—Uniform.
*Single berry weight*.—About 5.2 g.
*Shape*.—Rounded elliptic.
*Seeds*.—Absent.
*Cross section*.—Circular.
*Berry dimensions*.—longitudinal axis: About 2.3 cm. Horizontal axis: About 2.0 cm.
*Pedicel length*.—About 12 mm.
*Pedicel width*.—About 2.2 mm.
*Pedicel color*.—Yellow-green: 144C.
*Berry firmness*.—Moderately firm.
*Particular flavor*.—Neutral.
*Bloom* (*cuticular wax*).—Weak.
*Berry separation from pedicel*.—Medium difficult.
*Skin color* (*without bloom*).—Yellow-green: 151A.
*Flesh color*.—Yellow-green: 145D.

Skin:
*Thickness*.—Medium.
*Texture*.—Not notable when chewing.
*Reticulation*.—Absent.
*Tenacity*.—Tenacious to flesh.

What is claimed:

1. A new and distinct variety of grapevine as herein illustrated and described.

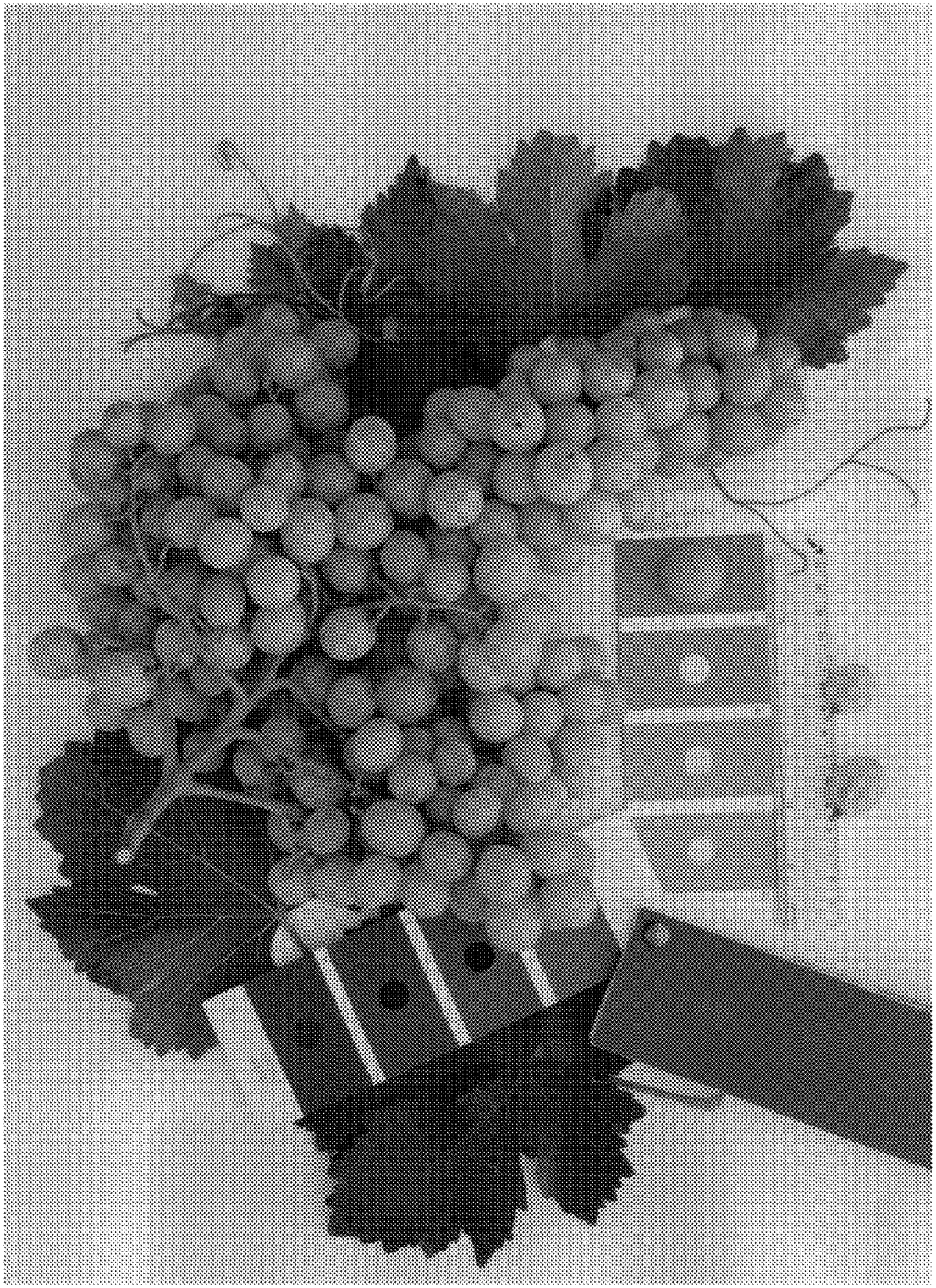

* * * * *